(12) United States Patent
Nolan et al.

(10) Patent No.: US 6,774,274 B2
(45) Date of Patent: Aug. 10, 2004

(54) METAL COMPLEXES FOR HYDROGENATION OF UNSATURATED COMPOUNDS

(75) Inventors: Steven P. Nolan, New Orleans, LA (US); Hon Man Lee, New Orleans, LA (US); Anna C. Hillier, New Orleans, LA (US)

(73) Assignee: University of New Orleans Research and Technology Foundation, Inc., New Orleans, LA (US)

( * ) Notice: Subject to any disclaimer, the term of this patent is extended or adjusted under 35 U.S.C. 154(b) by 217 days.

(21) Appl. No.: 10/011,680

(22) Filed: Dec. 4, 2001

(65) Prior Publication Data

US 2002/0173650 A1 Nov. 21, 2002

Related U.S. Application Data

(60) Provisional application No. 60/251,075, filed on Dec. 4, 2000, and provisional application No. 60/289,073, filed on May 7, 2001.

(51) Int. Cl.[7] .............................. C07C 5/00; C07C 5/02
(52) U.S. Cl. ..................... 585/705; 585/275; 585/259; 585/277; 556/137
(58) Field of Search ................................ 585/275, 259, 585/277, 705; 556/137

(56) References Cited

U.S. PATENT DOCUMENTS

| 5,728,839 | A | | 3/1998 | Herrmann et al. |
| 6,316,380 | B1 | * | 11/2001 | Nolan et al. ................. 502/155 |
| 6,552,139 | B1 | * | 4/2003 | Herrmann et al. ........... 526/171 |
| 6,613,910 | B2 | * | 9/2003 | Grubbs et al. ............... 548/103 |

OTHER PUBLICATIONS

Lee et al. A Cationic Complex Bearing an Imidazol–2–ylidene Ligand as Alkene Hydrogenation Catalyst. Organometallics, Feb. 2001, vol. 20, No. 6, pp. 1255–12–58, see entire document.

Hiller et al. Cationic Iridium Complexes Bearing Imidazol–2–ylidene Ligands as Transfer Hydrogenation Catalysts. Organometallics. Aug. 2001, vol. 20, No. 20, pp. 4246–4252, see entire document.

* cited by examiner

*Primary Examiner*—Walter D. Griffin
*Assistant Examiner*—Tam M. Nguyen
(74) *Attorney, Agent, or Firm*—Garvey, Smith, Nehrbass & Doody, L.L.C.; Seth M. Nehrbass

(57) ABSTRACT

The cationic iridium carbene complexes [Ir(cod)(N)(L)]X have been synthesized by reaction of [Ir(cod)(py)$_2$]PF$_6$ with L or NL ligands. Complexes of this type are active hydrogenation catalysts capable of hydrogenating simple olefins at room temperature and atmospheric pressure of hydrogen or by transfer hydrogenation.

15 Claims, 2 Drawing Sheets

METAL COMPLEXES FOR HYDROGENATION OF UNSATURATED COMPOUNDS

CROSS-REFERENCE TO RELATED APPLICATIONS

U.S. Provisional patent application serial No. 60/251,075, filed Dec. 4, 2000, is incorporated herein by reference. U.S. Provisional patent application serial No. 60/289,073, filed May 7, 2001, is incorporated herein by reference. Priority of both of these applications is hereby claimed.

STATEMENT REGARDING FEDERALLY SPONSORED RESEARCH OR DEVELOPMENT

This material is based upon work supported by the National Science Foundation (Contract No. 9985213) and the Petroleum Research Fund administered by the American Chemical Society under Grant No. ACS-PRF 35718-AC1. The US Government has certain rights in this invention.

Any opinions, findings, and conclusions or recommendations expressed in this material are those of the inventors and do not necessarily reflect the views of the National Science Foundation.

REFERENCE TO A "MICROFICHE APPENDIX"

Not applicable

BACKGROUND OF THE INVENTION

1. Field of the Invention

The present invention relates to hydrogenation catalysts. More particularly, the present invention relates to hydrogenation catalysts for olefins.

2. General Background of the Invention

Among homogenous hydrogenation catalysts, the most widely used are RhCl(PPh$_3$)$_3$ (Wilkinson's catalyst)[1] and [Ir(cod)(py)(PCy$_3$)]PF$_6$ [py=pyridine; cod=cyclooctadiene] (1, Crabtree's catalyst)[2]. The latter complex is an efficient catalyst for polysubstituted olefins lacking coordinating functionalities and is particularly useful in directed hydrogenation processes.[3] Despite having such remarkable catalytic activity, 1 has been shown to be susceptible to deactivation through the formation of inactive hydride-bridged trimer [(Ir(py)(PCy$_3$)(H$_2$))$_3$($\mu_3$-H)]PF$_6$, and has also been demonstrated as thermally unstable.[2a,c]

Nucleophilic N-heterocyclic carbenes, or so-called "phosphine mimics", have attracted considerable attention as possible alternatives for the widely used phosphine ligands in homogeneous catalysis.[4] Indeed, the inventors and others had found that the replacement of bulky phosphines with sterically demanding N-heterocyclic carbenes IPr (IPr=1,3-bis(2,6-diisopropylphenyl)imidazol-2-ylidene) (see FIG. 2) or IMes (IMes=1,3-bis(2,4,6-trimethylphenyl)imidazol-2-ylidene) (see FIG. 1) can result in significant catalytic performance in olefin metathesis,[5] C—C bond formation reaction,[6] animation of aryl chlorides,[7] hydrogenation[8] and hydroformylation[9].

The following U.S. patent is incorporated herein by reference: U.S. Pat. No. 5,728,839 for "Metal complexes with heterocycles carbenes" and all references recited therein and herein.

BRIEF SUMMARY OF THE INVENTION

Also incorporated by reference is the paper which describes an embodiment of the present invention, which was attached to U.S. Provisional patent application serial No. 60/251,075, filed Dec. 4, 2000, under the title "A Cationic Iridium Complex Bearing an Imidazolidine-2-ylidene Ligand as Alkene Hydrogenation Catalyst", and which was published in *Organometallics* (2001), vol. 20, no. 6, pp. 1255–1258 under the title: "A Cationic Iridium Complex Bearing an Imidazol-2-ylidene Ligand as Alkene Hydrogenation Catalyst".

In view of these findings and in their continued search for more efficient and stable catalysts, the inventors turned their attention to the Crabtree-type iridium hydrogenation catalyst. The inventors wished to examine whether the replacement of PCy$_3$ with SIMes (1,3-dimesityl-4,5-dihydroimidazol-2-ylidene or related n-heterocyclic carbenes, which is trivially called herein saturated IMes or SIMes) (see FIG. 3) in 1 could lead to the generation of a more active and more thermally tolerant hydrogenation catalyst. The present inventors now report the synthesis of a new iridium carbene complex [Ir(cod)(py)(SIMes)]PF$_6$ (2) and its catalytic behavior in the hydrogenation of olefins.

Attached to U.S. Provisional Patent Application Serial No. 60/289,073 and incorporated herein by reference is a copy of a manuscript entitled "Cationic Iridium Complexes Bearing Imidazol-2-ylidene Ligands As Transfer Hydrogenation Catalysts" which describes work on transfer hydrogenation using an Iridium catalyst. This paper has appeared in print as "Cationic Iridium Complexes Bearing an Imidazolidine-2-ylidene Ligand as Transfer Hydrogenation Catalysts." Hillier, A. C.; Lee, H. M.; Stevens, E. D.; Nolan, S. P. *Organometallics,* 2001, 20, 4246–4252. This is complementary to our earlier work involving hydrogenation with dihydrogen described in the paper which describes an embodiment of the present invention, which was attached to U.S. Provisional patent application serial No. 60/251,075, filed Dec. 4, 2000, under the title "A Cationic Iridium Complex Bearing an Imidazolidine-2-ylidene Ligand as Alkene Hydrogenation Catalyst", and which was published in *Organometallics* (2001), vol. 20, no. 6, pp. 1255–1258 under the title: "A Cationic Iridium Complex Bearing an Imidazol-2-ylidene Ligand as Alkene Hydrogenation Catalyst". Both of these papers, and all references recited therein, are also incorporated herein by reference.

The present invention includes hydrogenation with H atom sources other than hydrogen gas. This is what is so special about this discovery. Other examples exist but this is a fairly active system.

The present invention includes hydrogenation with dihydrogen and transfer hydrogenation (alcohols are source of H atoms).

The Ir catalysts described herein perform catalytic transfer hydrogenation using an inexpensive alcohol as the H atom source. The systems are versatile, hydrogenating both ketones and olefin. Very low catalyst loadings are required. The systems are very tolerant to elevated temperatures. The systems bear a nucleophilic carbene as ancillary ligand which affords a steric and electronic handle on the catalyst activity.

The present invention allows for either hydrogenation or transfer hydrogenation using inexpensive alcohols as the H atom source. The present catalyst systems allow both to be performed within essentially the same framework.

The new cationic iridium carbene complex [Ir(cod)(py) (SIMes)]PF$_6$ (2) has been synthesized by reaction of [Ir(cod) (py)$_2$]PF$_6$ with SIMes. Complex 2 is an active hydrogenation catalyst capable of hydrogenating simple olefins at room temperature and atmospheric pressure of hydrogen.

The cationic iridium carbene complexes [Ir(cod)(N)(L)]X have been synthesized by reaction of [Ir(cod)(py)$_2$]PF$_6$ with L or NL ligands. Complexes of this type are active hydrogenation catalysts capable of hydrogenating simple olefins at room temperature and atmospheric pressure of hydrogen or by transfer hydrogenation.

The present invention includes an iridium carbene complex of the formula [Ir(diene)(N)(L)]X. where diene is a diene or two monoene, N is a 2 electron nitrogen donor, L is a bulky nucleophilic carbene, and X is an anionic counterion. This complex is preferably prepared by a simple ligand exchange reaction of [Ir(diene)(N)2]X with L in toluene. Preferably an excess of L is used. The L can be prepared and used in situ by the reaction of L.HCl with KOBu$^t$ in THF, and the free carbene can be extracted with toluene and treated with [Ir(cod)(py)$_2$]PF$_6$ or equivalent precursors directly.

This complex can be used as a catalyst in a hydrogenation reaction in a method of hydrogenating simple olefins, comprising: The reaction can occurs at a pressure of 0.1 to 150 atmosphere and a temperature of 0–150° C.; for example, the reaction can occurs at a pressure of about 1 atm and a temperature of about 50° C.

The present invention includes an iridium carbene complex of the formula [Ir(cod)(py)(SIMes)]PF$_6$.; the complex can be prepared by a simple ligand exchange reaction of [Ir(cod)(py)$_2$]PF$_6$ with SIMes in toluene. Preferably, an excess of SIMes is used. The SIMes can be prepared and used in situ by the reaction of SIMes.HCl with KOBu$^t$ in THF, and the free carbene is extracted with toluene and treated with [Ir(cod)(py)$_2$]PF$_6$ directly. This complex can be used as a catalyst in a hydrogenation reaction for hydrogenating simple olefins.

The reaction can occur at a pressure of 0.1 to 150 atm and a temperature of 0 to 150° C. For example, the reaction can occur at a pressure of about 1 atm and a temperature of about 50° C.

The present invention comprises an olefin hydrogenation catalyst bearing a nucleophilic carbene ligand. This catalyst can be used as a catalyst in a hydrogenation reaction to hydrogenate simple olefins. This hydrogenation can occur with H atom sources other than hydrogen gas. For example, the hydrogenation can comprise transfer hydrogenation; in such a case, alcohol can be the source of H atoms.

The present invention also comprises a complex of the formula [Ir(cod)(py)(L)]PF$_6$, where L is from the group consisting of: IMes, 1,3-bis(2,4,6-trimethylphenyl)-imidazol-2-ylidene; IPr, 1,3-bis(2,6-di-iso-propylphenyl)-imidazol-2-ylidene; ICy, 1,3-bis(cyclohexyl)-imidazol-2-ylidene; and chiral carbene. This complex can be used as a catalyst for transfer hydrogenation reactions. This complex can be used as a catalyst in a method of hydrogenating simple olefins. The hydrogenation reaction can occur at a pressure of 0.1 to 150 atmosphere and a temperature of 0–150° C.; for example, the reaction can occur at a pressure of about 1 atm and a temperature of about 50° C. L can be ICy, 1,3-bis(cyclohexyl)-imidazol-2-ylidene.

The present invention also includes an iridium carbene complex of the formula [Ir(diene)(N-L)]X. where: diene is a diene or two monoene; N is a 2 electron nitrogen donor from the group consisting of oxazolines, phosphines, and carbenes; L is a bulky nucleophilic carbene; X is an anionic counterion; and N and L are tethered so N and L make a bidentate ligand. The two fragments can be tethered using a variety of subunits as known in the art. N can be an oxazoline so N-L is an oxazoline-carbene ligand; or N can be a phosphine so N—L is an phosphino-carbene ligand, or N can be a carbene and N-L is a bis-carbene ligand. A chiral version of the complex can be used as a catalyst in a method of catalyzing asymmetric hydrogenation reactions.

The present invention also can be characterized as an iridium carbene complex of the formula [Ir(diene)(R-C)]X. where: diene is a diene or two monoene; R—C is a chelating ligand; R is from the group consisting of phosphorus donors, oxygen donors, and nitrogen donors; C is a carbene; and X is an anionic counterion. R-C can be a chelating ligand from the group consisting of carbene-carbene, phosphine-carbene, and oxazoline-carbene. This complex can be used as a catalyst in a method of catalyzing hydrogenation reactions. The hydrogenation can be performed asymmetrically with a chelating ligand bearing a chiral center. The chelating ligand bearing a chiral center can be, for example, from the group consisting of chiral oxazoline-carbene, chiral phosphine-carbene, chiral carbene-oxazoline, chiral carbene-phosphine and chiral carbene-chiral carbene.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Results and Discussion

Synthesis and Characterization of [Ir(cod)(py)(SIMes)]PF$_6$ (2). Complex 2 was prepared by a simple ligand exchange reaction of [Ir(cod)(py)$_2$]PF$_6$ with SIMes in toluene (eq. 1).

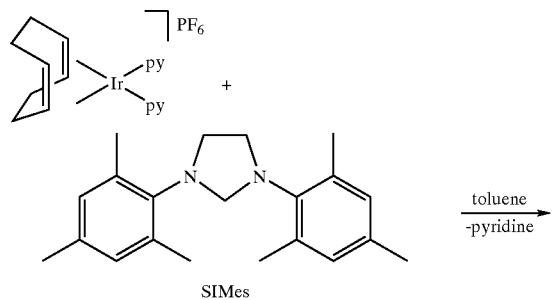

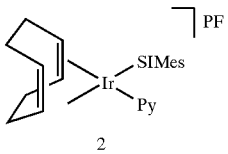

2

Due to the steric bulk of SIMes, this ligand could be used in slight excess to accelerate the kinetics of ligand substitution without fear of obtaining a dicarbene iridium complex. The free carbene was treated with [Ir(cod)(py)$_2$]PF$_6$ directly. After stirring at room temperature for 2 d, 2 was isolated as a yellow-orange solid in 80% yield. A similar methodology has been used by Grubbs to prepare a SIMes bearing ruthenium olefin metathesis catalyst.[5e]

The $^1$H NMR spectrum of 2 showed two multiplets at δ3.15 and 3.80 for the vinyl protons of the cod ligand. It has been previously demonstrated for [Ir(cod)(Cl)(L)]PF$_6$ (L=monophosphine) that the downfield signal can be assigned to the vinyl resonance trans to L (δ(H$_A$)). By analogy, the signal at δ3.80 can be assigned to vinyl protons trans to the SIMes and that at δ3.15 to the two vinyl protons trans to the pyridine ligand. Two mulitplets at δ3.78 and 3.96 were observed for the methylene protons of the SIMes ligand. In order to unequivocally establish the structure of 2, a single-crystal X-ray diffraction study was performed on crystals grown from slow diffusion of diethyl ether into a saturated dichloromethane solution of 2.

Figure 4:
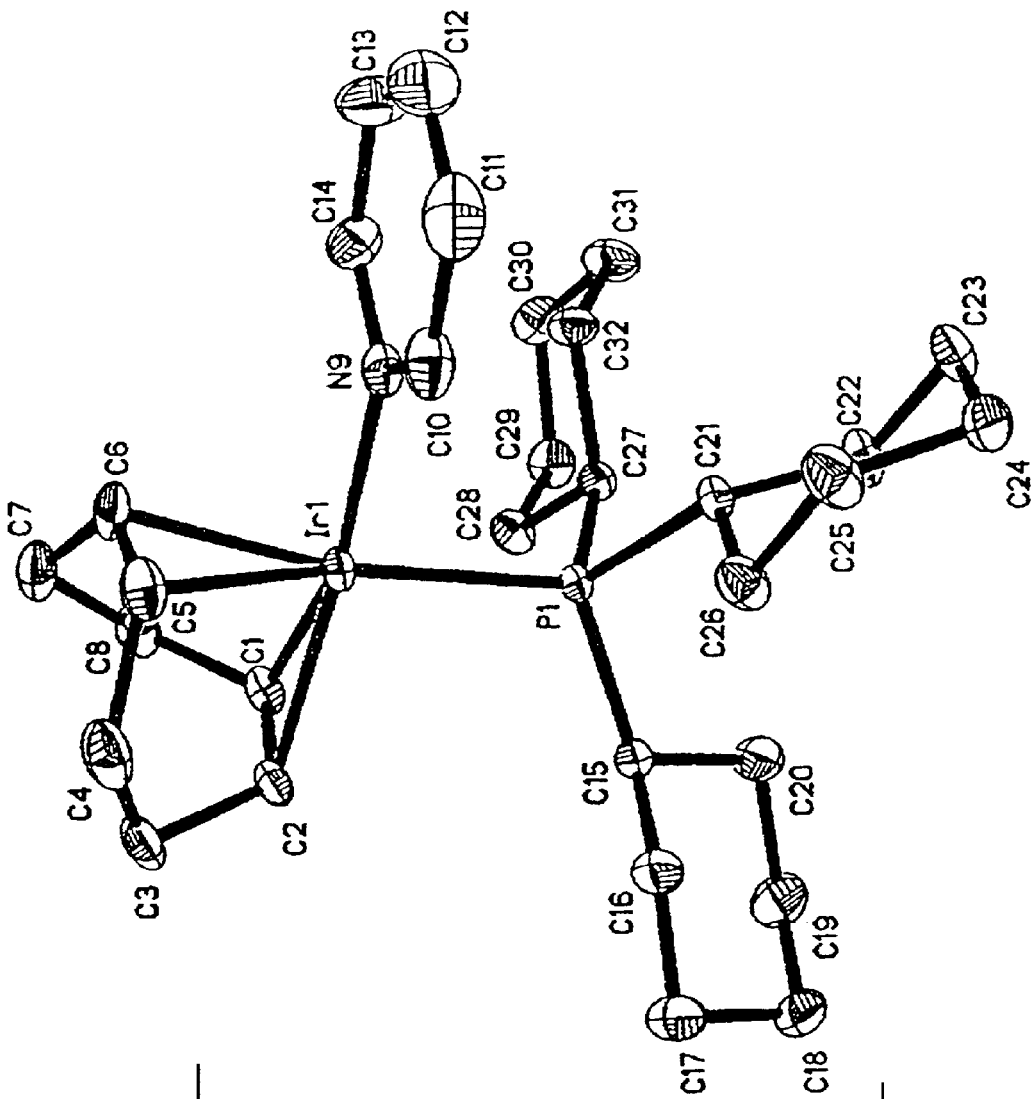
FIG. 4 is an ORTEP of [Ir(cod)(py)(SIMes)]PF$_6$ (2) with ellipsoids drawn in at 50% probability; hydrogens and PF$_6$ are omitted for clarity.
Figure 1:
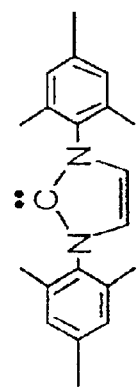
FIG. 1 shows a nucleophilic carbene IMes.
Figure 2:
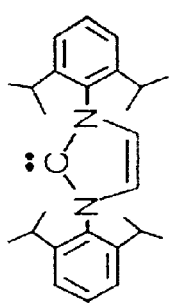
FIG. 2 shows a nucleophilic carbene IPr.
Figure 3:
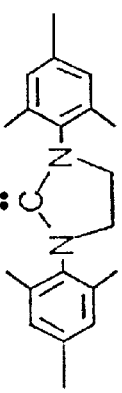
FIG. 3 shows a nucleophilic carbene SIMes.
Figure 5:
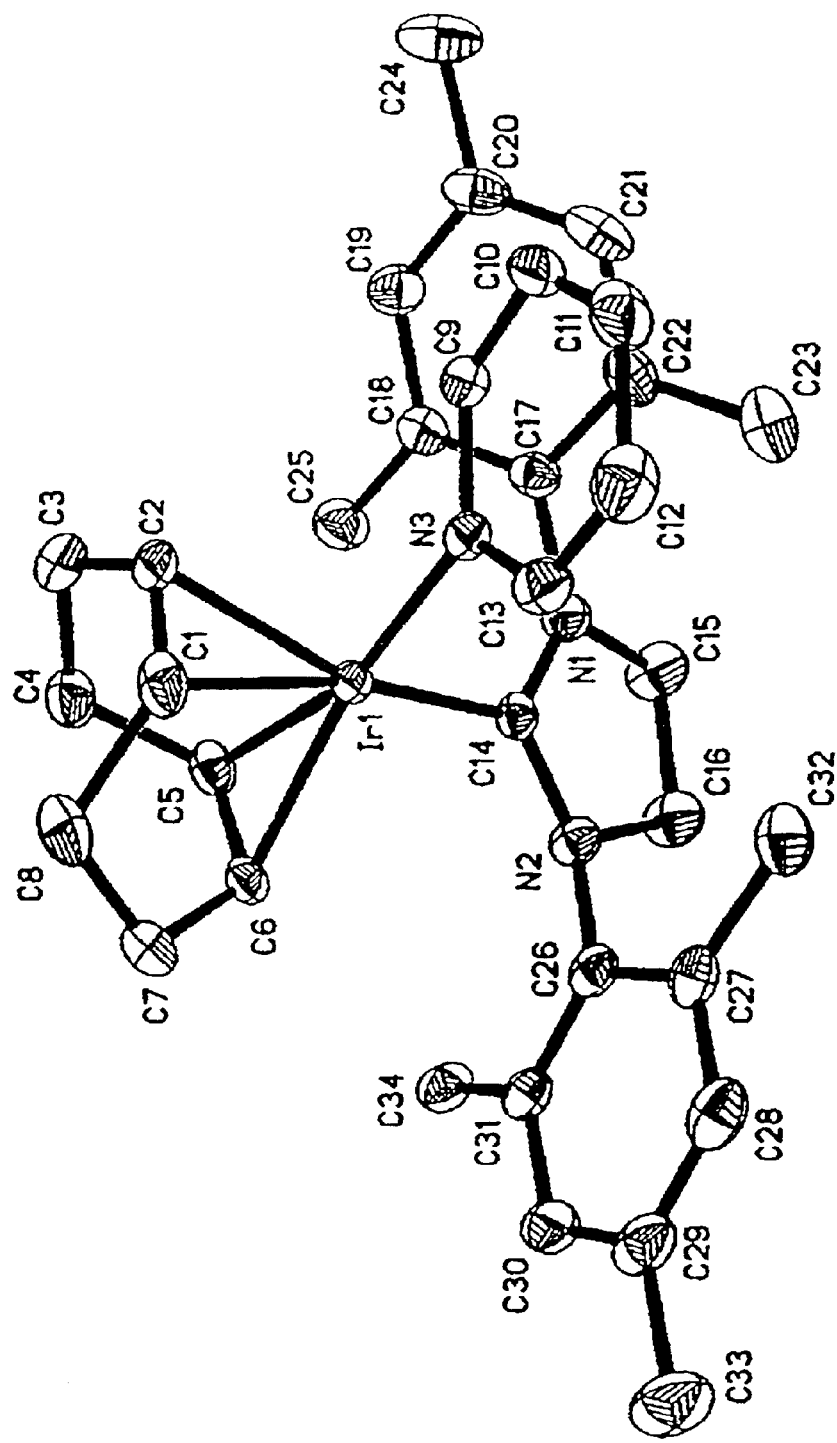
FIG. 5 is an ORTEP of [Ir(cod)(py)(PCy$_3$)]PF$_6$ (1) with ellipsoids drawn in at 50% probability; hydrogens and PF$_6$ are omitted for clarity.

Single Crystal X-ray Analysis of 1 and 2. As shown in the ORTEP (FIG. 4), 2 adopts a square-planar coordination geometry around the iridium center. The structure of 2 is very similar to that of 1, which had not previously been reported and is presented here for comparative purposes (FIG. 5).[10] Selected bond lengths and angles for 1 and 2 are given in Table 1. Consistent with the greater trans influences of SIMes and PCy$_3$ compared to pyridine, the Ir—C bond distances trans to the SIMes in 2 and PCy$_3$ in 1 are significantly longer than those trans to pyridine. This is also in accord with the vinyl protons assignments in the $^1$H NMR spectrum (vide supra). Previously, we showed that IMes was a stronger σ-donor than PCy$_3$,[5a] so it is reasonable to assume that the saturated analogue would also have a strong σ-donating capability. Consistently, the Ir—N bond distance in 2 (2.1073 Å) was longer than that found in 1 (2.089 Å) and the C═C bond distance trans to the SIMes in 2 was shorter than that trans to PCy$_3$ in 1 by 0.013 Å. A comparison of FIGS. 4 and 5 clearly illustrates the SIMes ligand in 2 occupying significantly more space around the iridium center than the PCy$_3$ ligand in 1.

Catalytic Hydrogenation. The catalytic performance of 2 in the hydrogenation of simple alkenes has been investigated. The catalytic activity of 1 was also studied for comparative purposes. Selected results are listed in Table 3. The catalytic reactions were performed with 1 mol % of catalyst in 5 mL of CH$_2$Cl$_2$. At ambient temperature and pressure of hydrogen, 2 was an efficient catalyst in the hydrogenation of cyclohexene, although displaying a lower activity than 1 (entry 1, 2). It is generally significantly more difficult to hydrogenate highly substituted alkenes. As shown in entry 3 and 4, Crabtree's catalyst gave a final 77% conversion of 1-methyl-1-cyclohexene while a modest yield of 44% was obtained when using 2. The catalytic reaction did not proceed to completion even after prolonged stirring when either 1 or 2 were employed. It had been shown that 1 undergoes an irreversible deactivation process over time involving the formation of the catalytic inactive hydrogen-bridged cluster (vide supra).

TABLE 1

Selected Bond Lengths (Å) and Angles (deg) for 1 and 2

| 1 | | 2 | |
|---|---|---|---|
| Bond Lengths | | | |
| Ir—P(1) | 2.3676(6) | Ir—C(14) | 2.0743(18) |
| Ir—N(9) | 2.089(2) | Ir—N(3) | 2.1073(16) |
| Ir—C(5) | 2.176(3) | Ir—C(1) | 2.215(2) |
| Ir—C(6) | 2.195(3) | Ir—C(2) | 2.1545(19) |
| Ir—C(1) | 2.145(3) | Ir—C(5) | 2.144(2) |
| Ir—C(2) | 2.163(3) | Ir—C(6) | 2.1349(18) |
| C(1)—C(2) | 1.407(4) | C(5)—C(6) | 1.408(3) |
| C(5)—C(6) | 1.404(4) | C(1)—C(2) | 1.391(3) |
| Bond Angles | | | |
| N(9)—Ir—P(1) | 92.17(7) | N(3)—Ir—C(14) | 96.00(7) |
| C(1)—Ir—P(1) | 92.46(8) | C(5)—Ir—C(14) | 89.71(8) |
| C(2)—Ir—P(1) | 97.70(8) | C(6)—Ir—C(14) | 93.00(7) |
| C(5)—Ir—N(9) | 85.67(11) | C(1)—Ir—N(3) | 88.21(7) |
| C(6)—Ir—N(9) | 86.90(11) | C(2)—Ir—N(3) | 86.93(7) |
| C(1)—Ir—N(9) | 156.23(10) | C(5)—Ir—N(3) | 164.45(7) |
| C(2)—Ir—N(9) | 162.39(10) | C(6)—Ir—N(3) | 154.58(8) |
| C(5)—Ir—P(1) | 160.95(8) | C(1)—Ir—C(14) | 169.80(8) |
| C(6)—Ir—P(1) | 161.43(9) | C(2)—Ir—C(14) | 152.16(9) |

Interestingly, 1 and 2 displayed different catalytic behaviors in the hydrogenation of 1-methyl-1,4-cyclohexene, which contains both a trisubstituted and a disubstituted non conjugated double bonds. Complex 1 gave a mixture of methylcyclohexane and 1-methyl-1-cyclohexene within 1 h (entry 5). The ratio of the fully hydrogenated to the partially hydrogenated product increased slowly over time until a final ratio of 84:16 was obtained. The isomeric, partially hydrogenated product, 1-methyl-4-cyclohexene was not observed. Presumably, 1 catalyzes a simple two-step process in which the first hydrogenation occurs at the less hindered double bond to form 1-methyl-1-cyclohexene, which is then converted to the fully hydrogenated methylcyclohexane in the subsequent step. Surprisingly, 2 gave a mixture of products, methylcyclohexane, 1-methyl-4-cyclohexene, and 1-methyl-1-cyclohexene in a ratio of 3:12:25 after 1 h (entry 6). The amount of 1-methyl-4-cyclohexene increased to a maximum after 4 h and then gradually decreased with time. The yield of the fully hydrogenated product increased slowly to a final 57% yield. These results showed that, in contrast to 1, the relative kinetics of hydrogenation of the least substituted and more substituted olefins are similar. Efforts directed at understanding the relative kinetics of these hydrogenation reactions are underway.

In an effort to determine the factors leading to an increase of the yield of the fully hydrogenated product for hindered substrates, we conducted catalytic hydrogenations of 1-methyl-1-cyclohexene under 60 psi of H$_2$ at 50° C. Since Crabtree's catalyst is not very thermally stable, it may not be surprising that its activity was drastically decreased when the catalytic reaction was conducted under 60 psi at 50° C. Catalyst degradation is presumably favored at elevated temperatures and conversion into a catalytically inactive species results in poor or no olefin hydrogenation. A poor 34% yield of methylcyclohexane was obtained after 7 h (entry 7) when using 1. In contrast, the activity of 2 is significantly improved under these conditions. In fact, a complete conversion to the fully hydrogenated product was obtained within 7 h (entry 8).

In summary, a new cationic iridium carbene complex 2 has been prepared and found to be effective in the hydrogenation of simple olefins. Although it is less efficient than Crabtree's catalyst at room temperature and atmospheric pressure of hydrogen, (which may be related to the larger steric bulk of SIMes in 2 compared to that of $PCy_3$ in 1), it displayed a higher activity under a mild pressure of hydrogen at 50° C. This is in contrast to the catalytic property of 1, which is significantly less active under the same conditions. The difference in activity can be attributed to the presence of the bulky N-heterocyclic carbene ligand in 2 which results in an improved thermal stability. Investigations into the use of the new catalyst to a variety of substrates and synthesis of a family of nucleophilic carbene bearing iridium complexes are ongoing.

Experimental Section

General Considerations. All reactions were carried out under an atmosphere of dry argon with standard Schlenk tube techniques or in a MBraun glovebox containing less than 1 ppm of oxygen and water. Anhydrous hexane was purchased from Aldrich and used as received. Toluene, THF, and $CH_2Cl_2$ were dried by passage through activated alumina columns.[11] The NMR solvents were dried from activated molecular sieves (4 Å). Complex 1 was purchased from Strem and used as received. [Ir(cod)(py)$_2$]PF$_6$[3a] and SIMes.HCl[12] were prepared according to the literature procedures. NMR spectra were recorded using a Varian 400 MHz spectrometer. Elemental analyses were performed by Desert Analysis, Tucson, Ariz. Gas chromatographic analyses were performed on a Hewlett-Packard HP 5890 II equipped with an FID and a HP-5 column.

Synthesis of [Ir(cod)(py)(SIMes)]PF$_6$ (2). A mixture of 423 mg SIMes.HCl (1.242 mmol) and 139 mg potassium tert-butoxide (1.242 mmol) in 20 mL of THF was stirred at room temperature for 1 h. The solvent was then removed completely under vacuum. The residue was extracted with 20 mL of toluene. The solution was filtered and charged with 500 mg of [Ir(cod)(py)$_2$]PF$_6$ (0.828 mmol). The suspension was then stirred at room temperature for 2 days. The orange precipitate was filtered on a collection frit, washed with hexane, and dried under vacuum. Yield: 550 mg (80%). Anal. Calcd for $C_{34}H_{43}F_6IrN_3P$: C, 49.15; H, 5.22; N, 5.60. Found: C, 49.35; H, 5.31; N, 5.80. $^1H$ NMR (399.95 MHz, $CD_2Cl_2$): δ1.60 (m, 4 H, $CH_2$ of cod), 1.90 (m, 4 H, $CH_2$ of cod), 2.33 (s, 3 H, $CH_3$), 2.36 (s, 6 H $CH_3$), 2.39 (s, 6 H, $CH_3$), 2.50 (s, 3 H, $CH_3$), 1.56 (m, 4 H, $CH_2$ of cod), 1.87 (m, 2 H, $CH_2$ of cod, 1.99 (m, 2 H, $CH_2$ of cod), 3.15 (m, 2 H, CH of cod trans to py), 3.78 (m, 2 H, $NCH_2CH_2N$), 3.80 (m, 2 H, CH of cod trans to SIMes), 3.96 (m, $NCH_2CH_2N$), 6.93–7.26 (m, 6H, aromatic H), 7.70–7.77 (m, 3 H, aromatic H). Crystals suitable for X-ray measurements were obtained by slow diffusion of ether into a dichloromethane solution of 2.

The hydrogenation experiments. A solution of 0.01 mmol of catalyst, 1.0 mmol of olefin in 5 mL of dichloromethane was loaded into a 50 ML scintillation vial equipped with a screw cap and septum inside a glove box. The vial was then purged with hydrogen from a Schlenk line for 1 min. The reaction was allowed to stir under atmospheric pressure of hydrogen and the product ratio was monitored by GC. In some of the cases, the catalytic solution was loaded into a 100 mL Fisher-Porter pressure bottle, which was purged with hydrogen three times and then pressurized with 60 psi of hydrogen. The reaction was allowed to stir in an oil bath at 50° C. for 7 h. The reaction flask was cooled to room temperature. The pressure was then carefully discharged and product ratios were determined by gas chromatography. Reported experimental yields are the average of two runs.

Acknowledgment. The National Science Foundation and the Petroleum Research Fund administrated by ACS are gratefully acknowledged for support of this work. Johnson Matthey is also gratefully acknowledged for their generous gift of [Ir(cod)Cl]$_2$.

Supporting Information Available: Tables of crystal data and structure refinement details, atomic coordinates, bond distances and angles, anisotropic thermal parameters, and hydrogen atom coordinates for 1 and 2. This material is available free of charge via the Internet at http://pubs.acs.org.

References and Notes (All Incorporated Herein by Reference)

1. Herrmann, W. A.; Cornils, B. *Angew. Chem., Int. Ed. Engl.* 1997, 36, 1049–1067.
2. (a) Crabtree, R. H.; Felkin, H.; Morris, G. E. *J. Organomet. Chem.* 1977, 135, 205–215. (b) Crabtree, R. H.; Morris, G. E. *J. Organomet. Chem.* 1977, 135, 395–403. (c) Crabtree, R. H. *Acc. Chem. Res.,* 1979, 12, 331–338. (d) Crabtree, R. H.; Felkin, H.; Fillebeen-Khan, T.; Morris, G. E. *J. Organomet. Chem.* 1979, 168, 183–195.
3. (a) Stork, G.; Kahne, D. E. *J. Am. Chem. Soc.* 1983, 105, 1072–1073. (b) Evans, D. A.; Morrissey, M. M. *Tetrahedron Lett.* 1984, 25, 4637–4640. (c) Schultz, A. G.; McCloskey, P. J. *J. Org. Chem.* 1985, 50, 5905–5907. (c) Crabtree, R. H.; Davis, M. W. *J. Org. Chem.* 1986, 51, 2655–2661. (d) Hoveyda, A.; Evans, D. A.; Fu, G. C. *Chem. Rev.* 1993, 93, 1307–1370. (e) Wender, P. A.; Badham, N. F.; Conway, S. P.; Floreancig, P. E.; Glass, T. E.; Gränicher, C.; Houze, J. B.; Jänichen, J.; Lee, D.; Marquess, D. G.; McGrane, P. L.; Meng, W.; Mucciaro, T. P.; Mühlebach, M. *J. Am. Chem. Soc.* 1997, 119, 2755–2756.
4. (a) Regitz, M. *Angew. Chem., Int. Ed. Engl.* 1996, 35, 725–728. (b) Hermann, W. A.; Köcher, C. *Angew. Chem., Int. Ed. Engl.* 1997, 36, 2162–2187. (c) Adruengo, A. J., III; Krafczyk, R. *Chem Zeit.* 1998, 32, 6–14 (d) Dullius, J. E. L.; Suarez, P. A. Z.; Einloft, S.; de Souza, R. F.; Dupont, J.; Fischer, J.; De Cian, A. *Organometallics* 1998, 17, 815–819. (e) Adruengo, A. J., III *Acc. Chem. Res.* 1999, 32, 913–921.
5. (a) Huang, J.; Stevens, E. D.; Nolan, S. P.; Petersen, J. L. *J. Am. Chem. Soc.* 1999, 121, 2674–2678. (b) Huang, J.; Schanz, H. J.; Stevens, E. D.; Nolan, S. P. *Organometallics* 1999, 18, 5375–5380. (c) Jafarpour, L.; Schanz, H. J.; Stevens, E. D.; Nolan, S. P. *Organometallics* 1999, 18, 5416–5419. (d) Scholl, M.; Trnka, T. M.; Morgan, J. P.; Grubbs, R. H. *Tetrahedron Lett.* 1999, 40, 336. (e) Scholl, M.; Ding, S.; Lee, C. W.; Grubbs, R. H. *Org. Lett.* 1999, 1, 953–956. (f) Chatterjee, A. K.; Grubbs, R. H. *Org. Lett.* 2000, 1, 1751–1753. (g) Bourissou, D.; Guerret, O.; Gabbaï, F. P.; Bertrand, G. *Chem. Rev.* 2000, 100, 39–91, and references therein.
6. (a) Zhang, C.; Huang, J.; Trudell, M. L.; Nolan, S. P. *J. Org. Chem.* 1999, 64, 3804–3805. (b) Böhm, V. P. W.; Gstöttmayr, C. W. K.; Weskamp, T.; Hermann, W. A. *J. Organomet. Chem.* 2000, 595, 186–190. (c) Huang, J.; Nolan, S. P. *J. Am. Chem. Soc.* 1999, 121, 9889–9890. (c) Lee, H. M.; Nolan, S. P. *Org Lett.* 2000, 2, 2053–2055.
7. Huang, J.; Grasa, G.; Nolan, S. P. *Org Lett.* 1999, 1, 1307–1309.
8. Lee, H. M.; Smith, D.C., Jr.; He, Z.; Stevens, E. D.; Yi, C. S.; Nolan, S. P. *Organometallics,* manuscript accepted for publication (copy attached to U.S. Provisional patent application serial No. 60/251,075, filed Dec. 4, 2000).
9. Chen, A. C.; Ren, L.; Decken, A.; Crudden, C. M. *Organometallics* 2000, 19, 3459–3461.

10. Orange crystals suitable for X-ray measurements were obtained by slow diffusion of ether into a dichloromethane solution of 1.
11. Pangborn, A. B.; Giardello, M. A.; Grubbs R. H.; Rosen, R. K.; Timmers, F. J. *Organometallics* 1996, 15, 1518–1520.
12. Arduengo, A. J., III; Krafczyk, R.; Schmutzler, R.; Craig, H. A.; Goerlich, J. R.; Marshall, W. J.; Unverzagt, M.; *Tetrahedron* 1999, 55, 14523–14534.

TABLE 2

Crystallographic Data for Complexes 1 and 2

| | 1 | 2 |
|---|---|---|
| formula | $[C_{31} H_{50} Ir P N]^+ PF_6^-$ | $[C_{34} H_{43} Ir N_3]^+ PF_6^-$ |
| fw | 804.86 | 830.88 |
| crystal system | triclinic | triclinic |
| space group | $P_1$ | $P_{-1}$ |
| a, Å | 9.5882(3) | 10.1394(2) |
| b, Å | 16.2726(4) | 12.4885(3) |
| c, Å | 10.3721(3) | 13.8435(3) |
| α, deg | 90.0000(10)° | 81.1310(10)° |
| β, deg | 103.2130(10)° | 74.43° |
| γ, deg | 90.0000(10)° | 80.4040(10)° |
| V, Å$^3$ | 1575.46(8) | 1653.94(6) |
| Z | 2 | 2 |
| $D_{calcd}$, Mg/m$^3$ | 1.697 | 1.668 |
| R | 0.0246 | 0.0231 |
| $R_w$ | 0.0267 | 0.0328 |
| no. of refined params | 571 | 513 |
| no. of data collected | 30173 | 32308 |
| no. of unique data, I > 3σ | 11317 | 11895 |
| $R_{merge}$ | 0.0318 | 0.0333 |

TABLE 3

Catalytic Hydrogenation of Olefins with Complexes 1 and 2.[a]

| entry | cat | substrate | time, h | yield,[b] % |
|---|---|---|---|---|
| 1 | 1 | cyclohexene | <0.5 | 100 |
| 2 | 2 | cyclohexene | 2 | 100 |
| 3 | 1 | 1-methyl-1-cyclohexene | 2 | 65 |
| | | | 28 | 77 |
| 4 | 2 | 1-methyl-1-cyclohexene | 3.5 | 42 |
| | | | 16 | 44 |
| 5 | 1 | 1-methyl-1,4-cyclohexene | 1 | 100 (63:0:35) |
| | | | 2 | 100 (76:0:24) |
| | | | 13 | 100 (84:0:16) |
| 6 | 2 | 1-methyl-1,4-cyclohexene | 1 | 40 (3:12:25) |
| | | | 4 | 93 (12:45:36) |
| | | | 7 | 100 (40:23:37) |
| | | | 18 | 100(57:4:39) |
| 7 | 1 | 1-methyl-1-cyclohexene | 7 | 34[c] |
| 8 | 2 | 1-methyl-1-cyclohexene | 7 | 100[c] |

[a]cat, 0.01 mmol; olefin, 1.0 mmol; $CH_2Cl_2$, 5 mL; $H_2$, 15 psi; temp, 25° C.
[b]The ratios in parentheses = (methylcyclohexane: 1-methyl-4-cyclohexane:1-methyl-1-cyclohexene). Yields are average of two runs.
[c]$H_2$, 60 psi; temp, 50° C.; time not optimized.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

What is claimed is:

1. A method of hydrogenating simple olefins, comprising:
   using as a catalyst in a hydrogenation reaction an iridium carbene complex of the formula [Ir(diene)(N)(L)]X, where diene is a diene or two monoene, N is 2 electron nitrogen donor, L is a bulky nucleophilic carbene, and X is an anionic counterion.

2. The method of claim 1, wherein the reaction occurs at a pressure of 0.1 to 150 atmosphere and a temperature of 0–150° C.

3. The method of claim 1, wherein the reaction occurs at a pressure of about 1 atm and a temperature of about 50° C.

4. A method of hydrogenating simple olefins, comprising:
   using as a catalyst in a hydrogenation reaction an iridium carbene complex of the formula [IR(cod)(py)(SIMes)] $PF_6$.

5. The method of claim 4, wherein the reaction occurs at a pressure of 0.1 to 150 atm and a temperature of 0 to 150° C.

6. The method of claim 4, wherein the reaction occurs at a pressure of about 1 atm and a temperature of about 50° C.

7. A method of hydrogenating simple olefins, comprising:
   using as a catalyst in a hydrogenation reaction an iridium carbene complex of the formula [IR(Cod)(py)(L)]$PF_6$, where L is from the group consisting of Imes, 1,3-bis (2,4,6,-trimethylphenyl)-imidazol-2-ylidene; Ipr, 1,3bis(2,6-di-iso-propylphenyl)-imidazol-2-ylidene; and chiral carbene.

8. The method of claim 7, wherein the reaction occurs at a pressure of 0.1 to 150 atmosphere and a temperature of 0–150° C.

9. The method of claim 7, wherein the reaction occurs at a pressure of about 1 atm and a Temperature of about 50° C.

10. The method of claim 7, comprising hydrogenation with H atom sources other than hydrogen gas.

11. The method of claim 7, comprising transfer hydrogenation.

12. The method of claim 7, comprising transfer hydrogenation in which alcohol is the source of H atoms.

13. A method of catalyzing hydrogenation reactions of olefin, comprising using as a catalyst an iridium carbene complex of the formula [Ir(diene)(R-C)]X, where
   diene is a diene or two monoene;
   R-C is a chelating ligand from the group consisting of carbene-carbene, phosphine-carbene, and oxazoline-carbene;
   R is from the group consisting of phosphorus donors, oxygen donors, and nitrogen donors;
   C is a carbene; and
   X is an anionic counterion.

14. The method of claim 13, wherein the hydrogenation is performed asymmetrically with a chelating ligand bearing a chiral center.

15. The method of claim 13, wherein the chelating ligand bearing a chiral center is from the group consisting of chiral oxazoline-carbene, chiral phosphine-carbene, chiral carbene-oxazoline, chiral carbene-phosphine and chiral carbene-chiral carbene.

* * * * *